US011944282B2

United States Patent
Reid et al.

(10) Patent No.: US 11,944,282 B2
(45) Date of Patent: Apr. 2, 2024

(54) ARTICULATION MECHANISMS AND METHODS OF USE

(71) Applicant: Boston Scientific Scimed, Inc., Maple Grove, MN (US)

(72) Inventors: Conor Reid, Cambridge, MA (US); Andrea Cahill, Cambridge, MA (US); Tara Ann Jarobski, North Oxford, MA (US); Paul Smith, Smithfield, RI (US); Tyler Cloyd, Boston, MA (US); Nestor Allan Ibanez, Brighton, MA (US); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 124 days.

(21) Appl. No.: 17/322,435

(22) Filed: May 17, 2021

(65) Prior Publication Data
US 2021/0353274 A1 Nov. 18, 2021

Related U.S. Application Data

(60) Provisional application No. 63/026,363, filed on May 18, 2020.

(51) Int. Cl.
| | | |
|---|---|---|
| A61B 17/00 | (2006.01) | |
| A61B 1/00 | (2006.01) | |
| A61B 1/018 | (2006.01) | |
| A61M 25/01 | (2006.01) | |

(52) U.S. Cl.
CPC .... *A61B 17/00234* (2013.01); *A61B 1/00133* (2013.01); *A61B 1/018* (2013.01); *A61B 2017/00323* (2013.01); *A61B 2017/00336* (2013.01); *A61B 2017/0034* (2013.01); *A61M 25/0136* (2013.01); *A61M 2025/015* (2013.01)

(58) Field of Classification Search
CPC .......... A61B 17/00234; A61B 1/00133; A61B 1/018; A61B 2017/00323; A61B 2017/00336; A61B 2017/0034; A61M 25/0136; A61M 2025/015
See application file for complete search history.

(56) References Cited

U.S. PATENT DOCUMENTS

| | | | |
|---|---|---|---|
| 6,743,185 B2 | 6/2004 | Weber et al. | |
| 7,566,300 B2 | 7/2009 | DeVierre et al. | |
| 7,762,960 B2 | 7/2010 | Timberlake et al. | |
| 9,149,274 B2 | 10/2015 | Spivey et al. | |
| 2003/0040657 A1 | 2/2003 | Yamaya et al. | |
| 2005/0096694 A1 | 5/2005 | Lee | |
| 2005/0234297 A1 | 10/2005 | DeVierre et al. | |
| 2009/0259141 A1* | 10/2009 | Ewers | A61B 1/018 600/106 |
| 2015/0257629 A1 | 9/2015 | Shahinian | |

FOREIGN PATENT DOCUMENTS

| | | |
|---|---|---|
| EP | 1839557 B1 | 1/2010 |
| WO | 97/12557 A1 | 4/1997 |
| WO | 2009/117696 A1 | 9/2009 |

* cited by examiner

*Primary Examiner* — Anh T Dang
(74) *Attorney, Agent, or Firm* — Bookoff McAndrews, PLLC

(57) ABSTRACT

An accessory device for use with a medical device includes a first cuff secured to a distal end of the medical device, a second cuff secured to the medical device proximal of the first cuff, an actuator, and at least one actuation wire extending from the first cuff, through the second cuff, to the actuator.

20 Claims, 8 Drawing Sheets

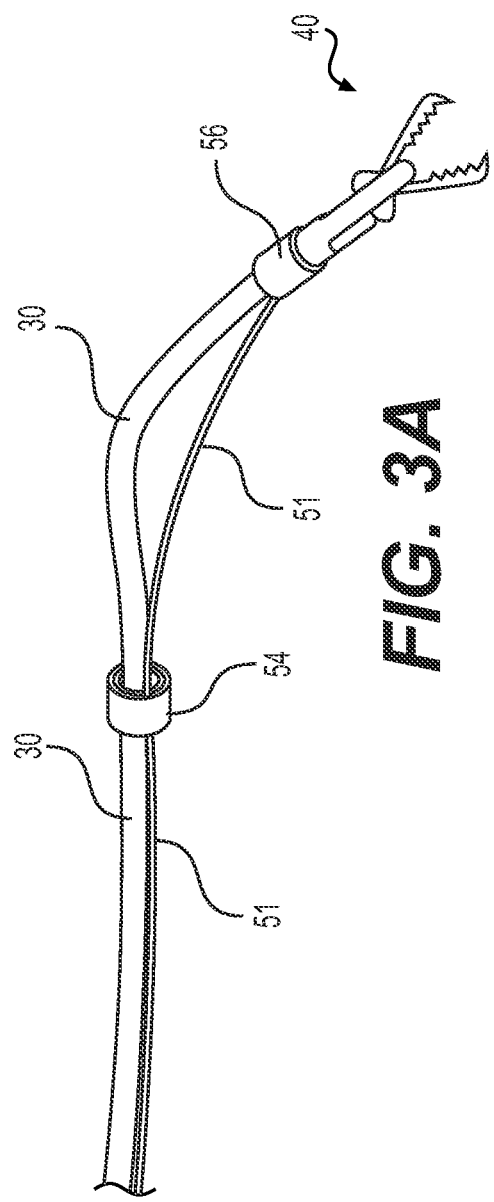
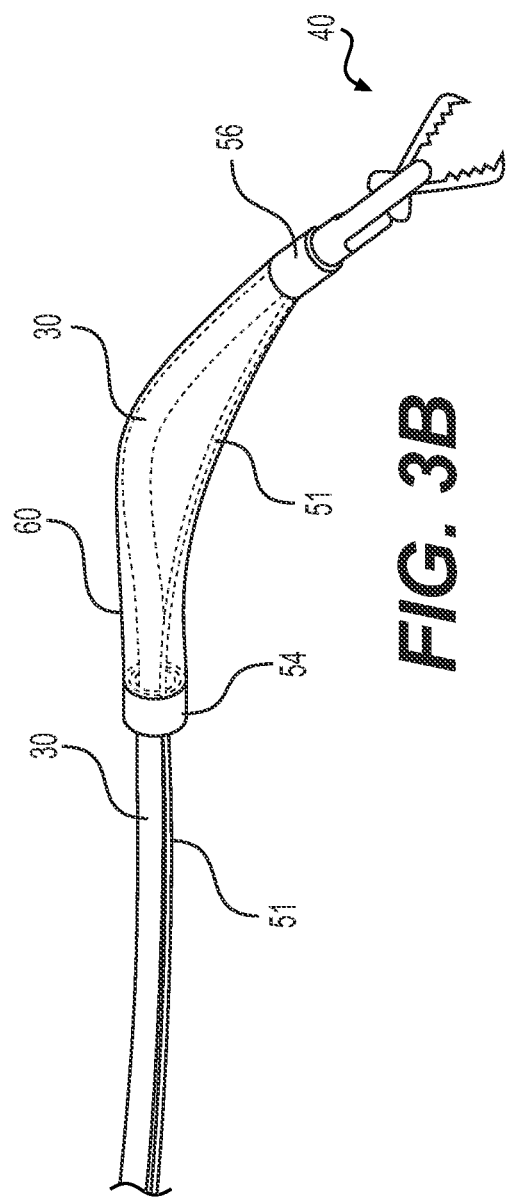

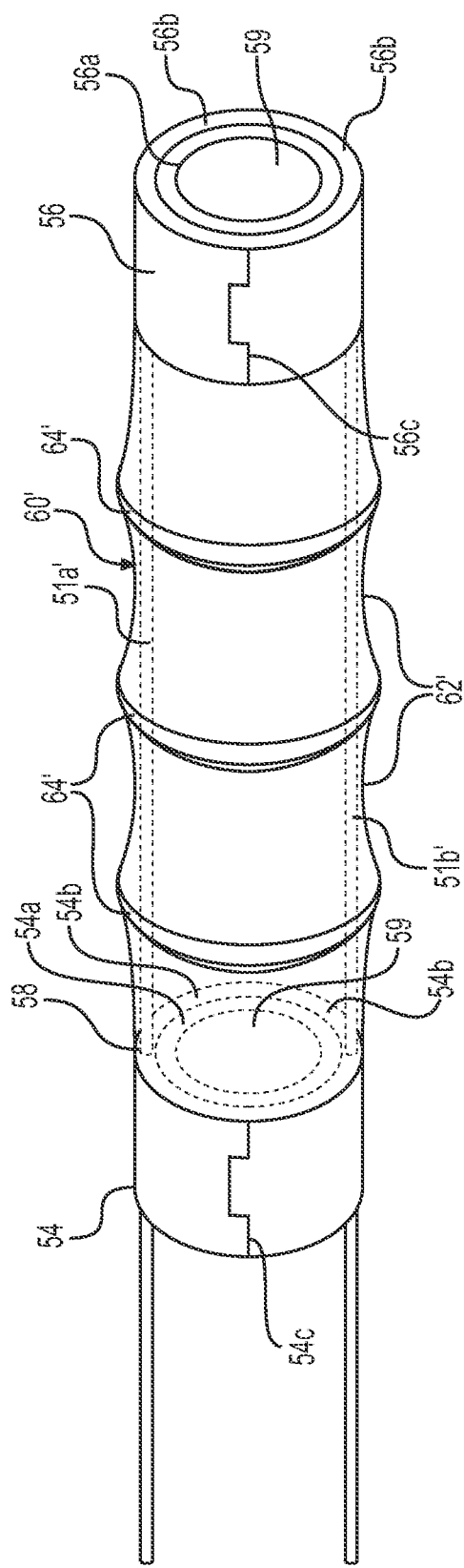
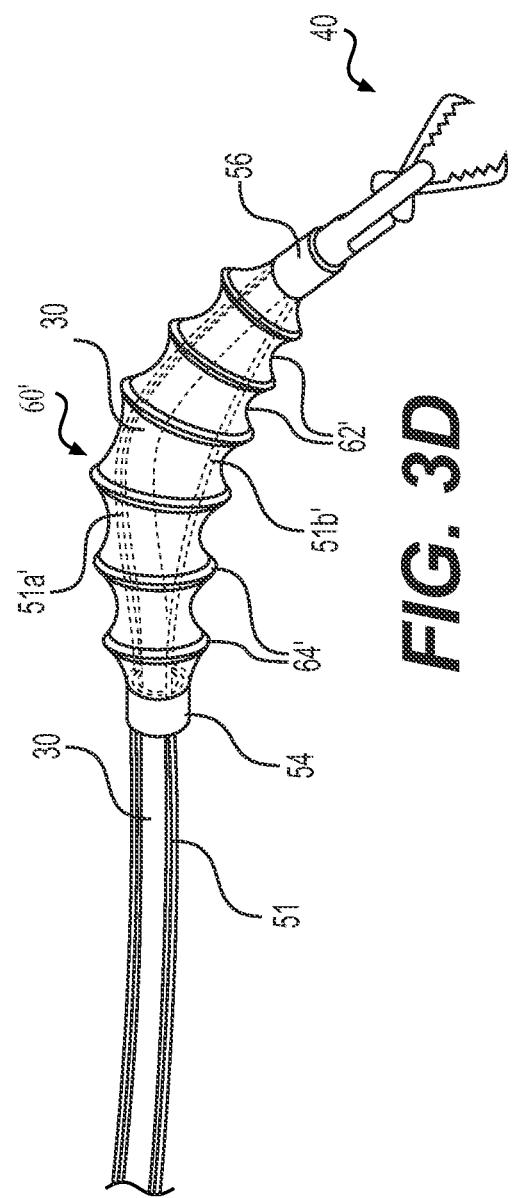
FIG. 3C
FIG. 3D

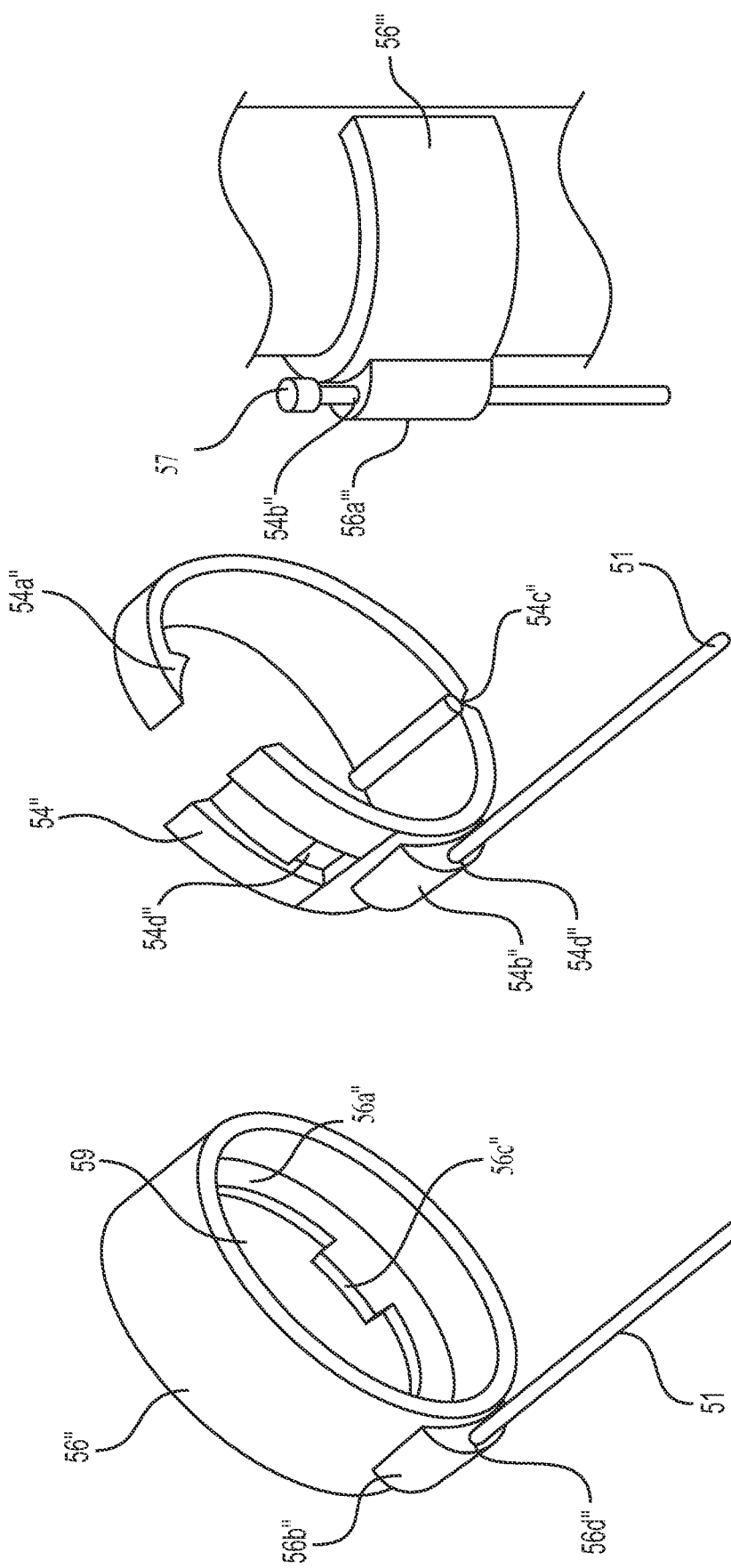

ARTICULATION MECHANISMS AND METHODS OF USE

CROSS-REFERENCE TO RELATED APPLICATIONS

This application claims the benefit of priority from U.S. Provisional Application No. 63/026,363, filed on May 18, 2020, which is incorporated by reference herein in its entirety.

TECHNICAL FIELD

This disclosure relates to endoscopic medical devices and methods of use. In some embodiments, the disclosure relates to an accessory device for one or more medical instruments (e.g., endoscopic accessory tools) associated with an endoscope for articulating the one or more medical instruments independent of actuating an articulation region of the endoscope.

BACKGROUND

Conventional medical instruments are generally advanced through a catheter, endoscope, or other like device, to a desired location in a patient. Endoscopes may include actuation mechanisms to articulate one or more regions of the endoscope to make passability through a tortuous path easier and/or to access a target site within the body. Articulation of medical instruments advanced within a lumen of the endoscope may be limited by the actuation and the articulation of the endoscope.

Accordingly, methods of performing medical procedures and medical instruments used in these procedures may require additional maneuverability. For example, when a medical instrument is advanced distally of a distalmost end of the endoscope, the maneuverability of the medical instrument is limited by the articulation of the endoscope. Thus, medical instruments used with conventional endoscopes may be unable to access certain areas of the body due to a tortuous path leading to the treatment site. This disclosure may solve one or more of these problems or other problems in the art. The scope of the disclosure, however, is defined by the attached claims and not the ability to solve a specific problem.

SUMMARY OF THE DISCLOSURE

According to an aspect, an accessory device for use with a medical device includes a first cuff configured to be secured to a distal end of the medical device, a second cuff configured to be secured to the medical device proximal of the first cuff, an actuator, and at least one actuation wire extending from the first cuff, through the second cuff, to the actuator.

One or more of the first cuff and the second cuff may include an outer member and an inner member, and wherein the outer member may be configured to compress the inner member against the medical device when one or more of the first cuff and the second cuff is secured to the medical device.

A material of the inner member may be configured to increase a friction between the inner member and the medical device.

The inner member may include one or more of a gel, a foam, or a plastic, and the outer member may include one or more of a metal, a ceramic, or an elastic material.

The accessory device may further include a membrane surrounding a portion of the medical device, wherein the membrane may extend between the first cuff and the second cuff.

The membrane may include a plurality of ridges separated by valleys.

The ridges may have a first thickness and the valleys may have a second thickness different than the first thickness The actuator may include a slot extending along a longitudinal axis of the actuator and an actuation mechanism configured to move within the slot, wherein the movement of the actuation mechanism within the slot may be configured to move the at least one actuation wire proximally and distally.

The second cuff may include an actuator lumen extending from a proximal end to a distal end, wherein the actuator lumen may be configured to receive the at least one actuation wire, and wherein the at least one second cuff may define an articulation joint about which the medical device is configured to bend.

The actuation wire may be fixed to the first cuff, and wherein the actuation wire may be configured to move within the actuator lumen and relative to the second cuff.

Movement of the actuation wire in the proximal direction may be configured to bend a portion of the medical device from a neutral position, in which the medical device lies along a longitudinal axis of the medical device, toward an articulated position angled relative to the longitudinal axis, and wherein movement of the actuation wire in the distal direction may be configured to move the portion of the medical device from the articulated position toward the neutral position.

One or more of the first cuff and the second cuff may include two portions, wherein the two portions may be joined together at adjacent first ends by a hinge.

The first cuff may include an annular ring extending from a sidewall of the first cuff toward a central axis of the first cuff, and wherein a projection may extend from a radially inwardmost edge of the annular ring toward the central axis.

At least one of the first cuff and the second cuff may be configured to contact a shoulder on a catheter of the medical device, and wherein a longitudinal movement of at least one of the first cuff or the second cuff in a proximal direction relative to the shoulder may be inhibited by contact between at least one of the first cuff or the second cuff and the shoulder.

At least one of the first cuff or the second cuff may be C-shaped, and wherein the at least one of the first cuff or the second cuff may extend only partially around a circumference of a catheter of the medical device when the accessory device is attached to the medical device.

According to another aspect, a medical device includes a catheter, a tool at a distal end of the catheter, and an accessory device, including a cuff secured to the catheter or the tool, a pivot member secured to the catheter proximal to the cuff, and an actuation wire fixed to the cuff, extending through the pivot member, and movable relative to the pivot member, wherein movement of the actuation wire relative to the pivot member is configured to articulate the catheter.

The medical device may further include a handle at a proximal end of the catheter, wherein the handle may include one or more actuators configured to operate the tool, and an actuation mechanism at a proximal end of the actuation wire, wherein movement of the actuation mechanism in a direction parallel to a longitudinal axis of the catheter may be configured to articulate the catheter.

The pivot member may include a distal end of a sheath, wherein the sheath may be disposed around the catheter, and wherein the sheath may be configured to be moved in a proximal direction or a distal direction to change a distance between the pivot member and the cuff.

According to another aspect, a method for performing an operation in a body may include advancing a delivery device to a target site via the endoscope, wherein the delivery device defines a lumen, introducing a medical tool into the lumen, wherein the medical tool includes a catheter, a tool at a distal end of the catheter, and an accessory device including a first member attached to a distal end of the medical tool, a second member attached to the catheter proximal of the first member, and an actuation wire extending from the first member, through the second member, to a proximal end of the accessory device; advancing the distal end of the medical tool distally to a distalmost end of the delivery device, and moving the actuation wire in a proximal direction to cause at least a portion of the catheter extending from the distalmost end of the endoscope to bend.

The method may further include moving the actuation wire in a distal direction after a completion of a medical procedure using the tool; and retracting the distal end of the medical tool proximally of the distalmost end of the delivery device.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3A is a perspective view of a distal end of the medical device of FIG. 1;

FIGS. 3B, 3C, and 3D are perspective views of a distal end of a medical device including an outer membrane;

FIGS. 5B, 5C, and 5D are perspective views of cuffs of an accessory device;

DETAILED DESCRIPTION

Figure 1:
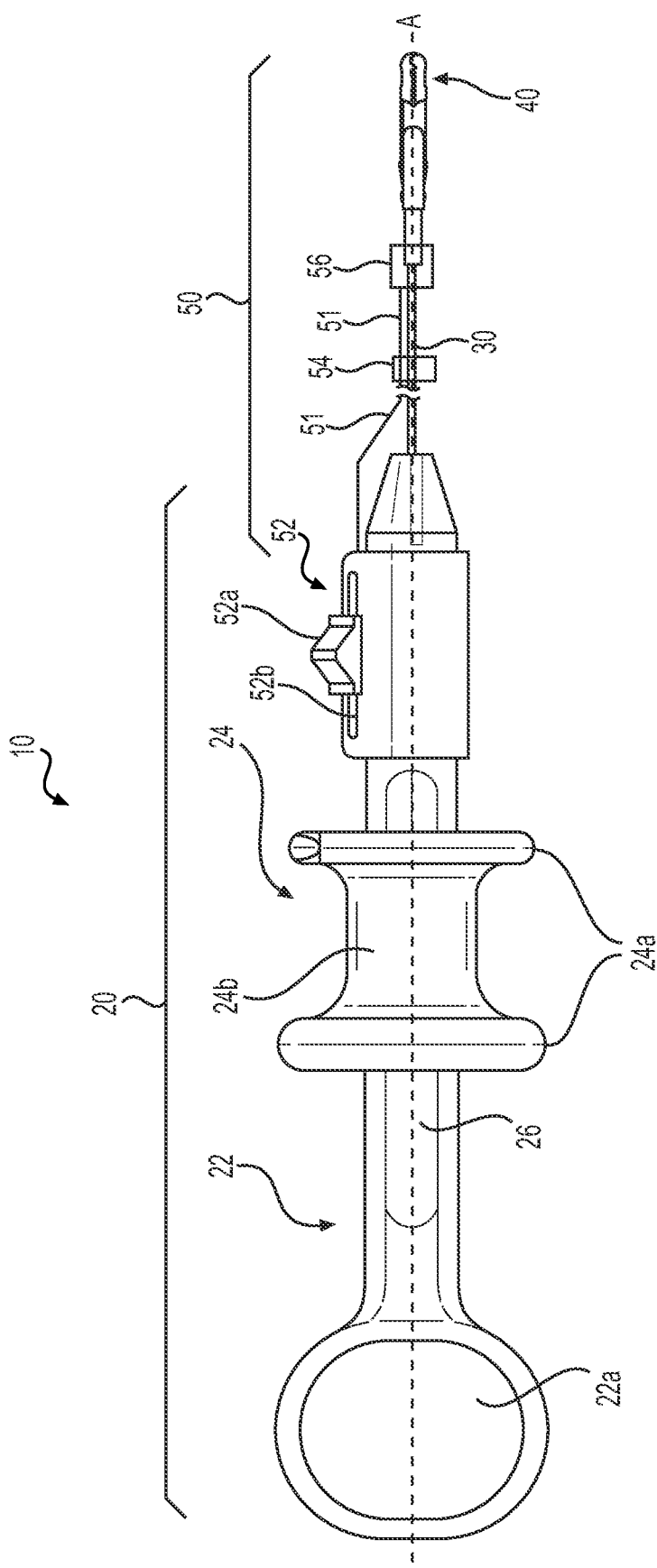
FIG. 1 is a schematic of a medical device according to an embodiment.

This disclosure is described with reference to exemplary medical systems and medical instruments or tools for accessing a target site, for example, for grasping, cutting, and/or stapling tissue. The medical instruments or tools may include an accessory device to allow the medical instruments or tools to be articulated independent from an endoscope or other catheter, sheath, or delivery device through which the medical instruments or tools may access the target site. This may provide improved medical tool functionality by, e.g., improving maneuverability of the medical instruments, improving access to target sites, and/or approaching target sites from different directions that may not be possible using only the endoscope, the catheter, or other delivery device. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. This disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately," and "substantially" indicate a range of values within +/−10% of a stated or implied value. Additionally, terms that indicate the geometric shape of a component/surface refer to exact and approximate shapes.

Embodiments of this disclosure may be used to perform a medical procedure on a tissue in an endo-luminal space, or facilitate the process thereof. According to an example, medical instruments may include an end effector having a resection or cutting mechanism (e.g., an integrated knife), a stapling mechanism (e.g., a stapler), a suction mechanism, a grasping mechanism, a biopsy mechanism, or any other tool used in a medical procedure. The medical instrument may be delivered through an endoscope working channel to the target tissue site. All or parts of the medical instrument could be metallic (such as stainless steel, titanium, or cobalt chrome), plastic (such as polyetheretherketone (PEEK) or the like), or include a shape memory metal (such as Nitinol), a shape memory polymer, a polymer, or any combination of materials. While reference is made herein to an accessory device for use with a medical instrument including a biopsy device with a control mechanism, the described accessory device may be used with any medical instrument, and the medical instrument may be used with or without an endoscope. The accessory device may provide improved articulation of a medical instrument. For example, the accessory device may directly articulate the medical instrument, whereas articulation of an endoscope may change the path (e.g., lumen) through which the medical instrument may travel.

Referring to FIG. 1, a medical instrument 10 according to an embodiment is shown. Medical instrument 10 includes a handle 20, a catheter 30 connected to handle 20, and an end effector assembly 40 (e.g., a biopsy assembly) at a distal end of catheter 30, opposite handle 20. An accessory device 50 is attached to handle 20, catheter 30, and end effector assembly 40, as will be described herein. As used herein, an end effector or end effector assembly 40 may be any tool or mechanism at a distal end of catheter 30. Accessory device 30 may be removable, e.g., may be attached to and removed from a medical instrument, and accessory device 30 may be used with multiple medical instruments during a medical procedure. Medical device 10 may be any device having an end effector, e.g., biopsy forceps, scissors, a needle, a snare, a stapler, or other medical end effector.

Handle 20 includes a body 22 defining a hole 22a in body 22 at a proximal end thereof. Catheter 30 is attached at an opposite, distal end of body 22. A slot 26 extends through body 22 in a direction parallel to a longitudinal axis A of medical instrument 10. A spool 24 is disposed in slot 26 and moves within slot 26 and along body 22 in a direction parallel to longitudinal axis A. Spool 24 includes two annular protrusions 24a at a distal end and a proximal end thereof and extending from spool 24 in a direction perpendicular to the direction of longitudinal axis A and the extension of catheter 30. Annular protrusions 24a define an annular grip 24b, which is grasped by a user. For example, a user may place a thumb or a finger in hole 22a and may grasp annular grip 24b with two fingers (e.g., the index and middle fingers). The user may move spool 24 proximally and distally along slot 26 to actuate end effector assembly 40, as discussed herein. It will be understood that handle 20 may be made of any material known in the art, including, but not limited to, a medical grade plastic or rubber, a ceramic, a metal, or a combination thereof. It will also be understood that handle 20 is not limited to the configuration shown in FIG. 1. For example, handle 20 may be any actuating handle known in the art, including, but not limited to, the devices disclosed in U.S. Pat. No. 6,743,185 and/or U.S. Pat. No. 7,762,960, the contents of each of which are incorporated herein by reference in their entirety.

An actuation wire (not shown) extends distally from the distal end of spool 24. The actuation wire extends through a hole (not shown) at the distal end of body 22 and into a lumen (not shown) of catheter 30. Actuation of the actuation wire actuates end effectors (e.g., biopsy jaws, cutting members, or grasping members) of end effector assembly 40. For example, as spool 24 moves proximally and distally, the actuation wire is moved proximally and distally and actuates end effector assembly 40 (e.g., by opening or closing jaws of a biopsy device, actuating a needle, or the like). As will be understood, catheter 30 is a generally circular sheath extending from handle 20 along longitudinal axis A, with end effector assembly 40 extending from a distal end thereof. While catheter 30 is described as including a lumen (not shown), catheter 30 may include multiple lumens to accommodate other actuators, wires, and/or lighting or imaging elements. Additionally, or alternatively, catheter 30 may be placed in another, larger catheter endoscope, colonoscope, bronchoscope, ureteroscope, sheath, or other like-device (not shown), if use of tools, suction, light-emitting elements, imaging, or the like associated with the larger catheter are desired. It will be understood that the wire may include any material known in the art, including, but not limited to, medical grade plastic, metal, or other resin suitable for actuating and/or maneuvering end effector assembly 40, as described herein, during medical procedures. Further, it will be understood that catheter 30 may be formed of any medical grade plastic, rubber, resin, or the like that is suitable for use in medical applications.

Figure 2:
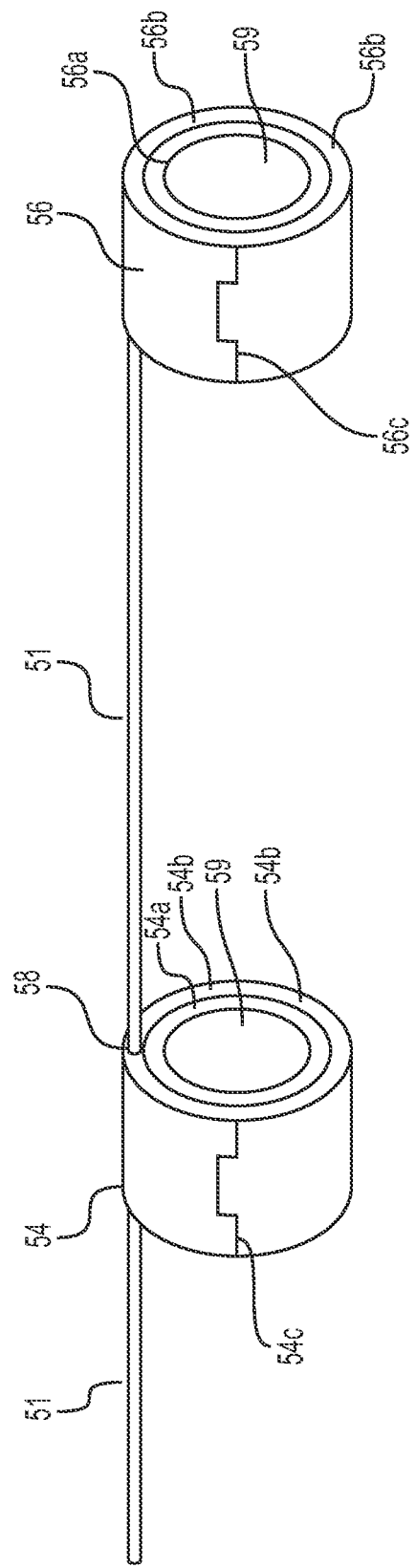
FIG. 2 is a perspective view of an accessory device for use with the medical device of FIG. 1.

As shown in FIGS. 1 and 2, accessory device 50 includes an actuator 52, first and second cuffs 56, 54, and an actuation wire 51. First cuff 56 may be attached at a distal end of medical instrument 10, e.g., may be attached to or attached adjacent to end effector assembly 40. Second cuff 54 may be attached to medical instrument 10 proximal to first cuff 56. For example, second cuff 54 may be attached to catheter 30 at a location proximal to first cuff 56. Actuation wire 51 may extend proximally from first cuff 56 to actuator 52, via second cuff 54. A distal end of actuation wire 51 may be attached to first cuff 56, and a proximal end of actuation wire 51 may be attached to actuation mechanism 52a. While actuation wire 51 is shown as being a rigid member with, e.g., angled surfaces, it will be understood that actuation wire 51 may be non-rigid and may be, e.g., a cable or the like. Further, actuation wire 51 may be cylindrical, flat, or any other shape suitable for use with medical devices.

As shown in FIG. 1, actuator 52 may be attached to a body of handle 20 via a snap fit, adhesive connection, or the like. For example, actuator 52 may be back fed over end effector assembly 40 and catheter 30, until actuator 52 reaches handle 20. Actuator 52 may lie over a distal end of handle 20 and remain positioned thereon via a friction fit. Alternatively, actuator 52 may be independent from handle 20 and may be grasped by the user's other hand or by another user. Actuation mechanism 52a may protrude through a channel 52b in a surface of actuator 52 and may move along channel 52b. For example, channel 52b may extend from a distal end of actuator 52 to a proximal end of actuator 52 along longitudinal axis A of medical instrument 10. Actuation mechanism 52a may include a triangular, knob, slider, protrusion, raised surfaces, and/or other shapes to provide a mechanism by which the user may grasp and actuate actuation mechanism 52a. Interaction with actuation mechanism 52a, e.g., by a user's thumb or finger, may allow the user to slide actuation mechanism 52a along channel 52b. Movement of actuation mechanism 52a along channel 52b may cause actuation wire 51 to move proximally and distally and may cause medical instrument 10 to articulate, as will be described herein.

A distal end of accessory device 50 is shown in FIG. 2. First cuff 56 is approximately cylindrical. First cuff 56 defines a lumen 59 and includes an inner member 56a and an outer member 56b. First cuff 56 may be a ring-shaped member and/or may have a clam-shell configuration. For example, first cuff 56 may include two halves connected by a hinge or clasp 56c (e.g., a pivot pin), which defines a pivotal axis. The two halves of first cuff 56 may pivot relative to each other about clasp 56a. This may enable first cuff 56 to be attached and/or removed from medical instrument 10. First cuff 56 may also include a hole or recess (not shown) which may receive a distal end of actuation wire 56. The distal end of actuation wire 51 may be fixed in the recess, e.g., via an adhesive, welding, or the like. Alternatively, the distal end of actuation wire 51 may be attached directly to an outer member of first cuff 56. While only one actuation wire 51 is illustrated, any number of actuation wires 51 may be provided. For example, two, three, four, or more actuation wires 51 may be attached to the proximal end of first cuff 56 and spaced equally about a circumference of first cuff 56.

Inner member 56a is cylindrical and may be include a material that may compress and/or that may increase the friction coefficient between first cuff 56 and catheter 30 or end effector assembly 40. For example, inner member 56a may be a gel, a foam, a plastic, or the like. Outer member 56b may include a more rigid metal, a ceramic, or other material that may compress the material of inner member 56a when first cuff 56 is attached to catheter 30. For example, when first cuff 56 is attached to catheter 30, outer member 56b may compress inner member 56a, which may inhibit movement of first cuff 56 relative to catheter 30. Alternatively, first cuff 56 may slide onto catheter 30 from the distal end. Proximal movement of first cuff 56 along catheter 30, e.g., longitudinal displacement in a proximal direction, may be prevented based on a diameter of catheter 30. For example, catheter 30 may be tapered from the proximal end to the distal end. Once the outer diameter of catheter 30 is greater than an inner diameter of first cuff 56, proximal movement of first cuff 56 may be prevented. As yet another example, outer member 56b may include a rubberband like material that may compress around inner member 56a to prohibit movement of first cuff 56 along catheter 30.

Second cuff 54 may have a similar structure as first cuff 56. For example, second cuff 54 may have an inner member 54a and an outer member 54b. Inner member 54a may include a same or similar material as inner member 56a, and outer member 54b may include a same or similar material as outer member 56b. Second cuff 54 may also define a lumen 59. Second cuff 54 may also be a ring-shaped member and/or may include two halves attached in a clam shell configuration. For example, a hinge or clasp 54c may define a pivot axis and may join two halves of outer member 54b. Similar to first cuff 56, the two halves of second cuff 54 may rotate about the pivot axis defined by clasp 54c when attaching or detaching second cuff 54 to catheter 30. For example, outer member 54b may compress inner member 54a against catheter 30, as discussed above relative to first cuff 56. Alternatively, similar to first cuff 56, an inner diameter of second cuff 54 may have a diameter smaller than an outer diameter of a portion of catheter 30. In this manner, proximal movement of second cuff 54 may be prevented once second cuff 56 reaches a position on catheter 30 where the outer diameter of catheter 30 is greater than the inner diameter of second cuff 54.

Second cuff 54 also includes an actuator lumen 58 extending from a distal end to a proximal end of second cuff 54. Actuator lumen 58 may be formed in outer member 54b or inner member 54a. Actuation wire 51 may pass through actuation lumen 58 toward actuator 52, and actuation wire 51 may move longitudinally within actuation lumen 58 relative to first cuff 54 (e.g., second cuff 54 may slide over wire 51). While a single actuator lumen 58 is shown, it will be understood that two, three, four, or more actuator lumens may be included based on the number of actuation wires 51.

FIG. 3A illustrates accessory device 50 attached to the distal end of catheter 30. First cuff 56 is attached at the distal end of catheter 30. Alternatively, first cuff 56 may be attached directly to end effector assembly 40. Second cuff 54 is attached to catheter 30 at a position proximal to first cuff 56. During operation, proximal movement of actuation wire 51 may cause tension on first cuff 56 and cause catheter 30 to articulate from a neutral position (e.g., lying along longitudinal axis A), about second cuff 54. Second cuff 54 acts as an articulation pivot, and catheter 30 bends between cuffs 54, 56. Distal movement of actuation wire 51 may cause first cuff 56 to articulate to move catheter 30 from a position offset from longitudinal axis A back to the neutral position. In some instances, catheter 30 may include a shape memory material that may be designed to arrange catheter 30 in the neutral position absent a force, e.g., a force from actuation wire 51 acting on cuffs 54, 56. In this instance, removing a proximal force from actuation wire 51 may cause catheter 30 to move toward the neutral position.

A distance between first cuff 56 and second cuff 54 may determine a bend radius of the portion of catheter 30 between cuffs 54, 56. For example, if the distance between first cuff 56 and second cuff 54 is small, the fine tune articulation control of catheter 30 will be greater than if the distance between first cuff 56 and second cuff 54 is large. Further, the bend radius of the portion of catheter 30 between cuffs 54, 56 will increase as the distance between first cuff 56 and second cuff 54 increases.

While only first and second cuffs 56, 54 are shown, it will be understood that more than two cuffs, e.g., three, four, or more cuffs, may be used. First cuff 56, e.g., a distalmost cuff, is fixed to the distal end of actuation wire 51. The remaining cuffs, e.g., a plurality of second cuffs 54, may each include an actuator lumen 58 for receiving actuation wire(s) 51. Additional cuffs may alter the bend radius and/or the ability to control the articulation of catheter 30. For example, additional cuffs may provide additional points about which catheter 30 may be articulated.

A method of operating medical instrument 10 using accessory device 50 will now be explained. Accessory device 50 may be attached to catheter 30. For example, first cuff 56 may be attached to the distal end of catheter 30 by clasping the two halves of outer member 56b to catheter 30. Second cuff 54 is attached to catheter 30 in a similar manner. In some instances, inner members 54a, 56a may be positioned on catheter 30 prior to clasping first and second cuffs 54, 56 over inner members 54a, 56a. Alternatively, inner members 54a, 56a may be attached to outer members 54b, 56b via adhesive or the like. In this manner, outer members 56b, 54b may compress inner members 56a, 54a, respectively, against catheter 30. As another example, first and second cuffs 54, 56 may be positioned on catheter 30 by inserting the distal end of catheter 30 through lumen 59 of respective first and second cuffs 54, 56. A friction force between first and second cuffs 54, 56, and catheter 30 may prevent movement of first and second cuffs 54, 56 along catheter 30 once first and second cuffs 54, 56 are positioned on catheter 30.

Once accessory device 50 is attached to catheter 30, the distal end of catheter 30 through may be introduced to the body through an incision or a natural orifice, e.g., via the mouth or the anus. In some instances, the distal end of catheter 30 may be inserted into a delivery device (e.g., a duodenoscope or other scope). The distal end of catheter 30 is advanced to a target site. During advancement, or after the distal end of catheter 30 has reached the target site, actuator 52 may be actuated by a user. For example, a user, using a finger or a thumb, may move actuation mechanism 52a in a distal direction and/or a proximal direction within channel 52b. As actuation mechanism 52a is moved, the distal end of catheter 30 is articulated. For example, as actuation mechanism 52a is moved proximally, the distal end of catheter 30 is articulated from a neutral position to an articulated position. When actuation mechanism 52a is moved distally, the distal end of catheter 30 is moved from the articulated position to the neutral position. Alternatively, or additionally, catheter 30 may move toward the neutral position based on the material of catheter 30, e.g., a shape memory material, absent a proximal force applied on actuation wire 51.

When using a delivery device (e.g., a duodenoscope or other scope), actuation of accessory device 50 occurs after the distal end of medical instrument 10 exits a distalmost end of the delivery device. In this manner, articulation of medical instrument 10 may be controlled independent of the delivery device. Alternatively, in the situation where the delivery device is not used for introducing medical instrument 10, e.g., if catheter 30 has sufficient rigidity, accessory device 50 may be used to articulate medical instrument 10 during insertion and/or after end effector assembly 40 reaches the target site. In this manner, medical instrument 10 may be capable of navigating a tortuous path, and/or accessing or approaching the target site from directions that may be not available using the delivery device alone.

FIG. 3B illustrates another example of accessory device 50 including a membrane 60. Membrane 60 may be a pliable or a semi-pliable covering and may be ultrathin (e.g., a thickness of approximately 0.001 inches to approximately 0.010 inches). Membrane 60 may extend from a proximal end of first cuff 56 to a distal end of second cuff 54, and connect first cuff 56 to second cuff 56. Alternatively, membrane 60 may extend from a distal end of first cuff 56 to a proximal end of second cuff 54, thereby covering cuffs 54, 56. Membrane 60 surrounds catheter 30 and actuation wire 51 and, in some embodiments, may restrict an outward movement of actuation wire 51, e.g., a movement away from catheter 30. Membrane 60 may prevent actuation wire 51 from contacting a body wall during actuation of accessory device 50. According to an example, an outer diameter of a fully expanded membrane of membrane 60 may be approximately twice an outer diameter of catheter 30. Membrane 60 may be any flexible material suitable for use in medical procedures, e.g., a silicone, a rubber, a plastic, or the like.

FIG. 3C illustrates another example of a membrane 60'. In this instance, membrane 60' may be a bellows or other similar device, and may have a thickness the same as or greater than that of membrane 60, e.g., approximately 0.001 inches to approximately 0.010 inches. According to this example, a pair of actuators 51a', 51b' extend from handle 20 to first cuff 56 via second cuff 54. Membrane 60' may also extend from first cuff 56 to second cuff 54 (as in the FIG. 3B example), and may include a plurality of ridges 64' and valleys 62', defined between adjacent ridges 62'. Ridges 64' may comprise thicker or more rigid material than the material between ridges 64' (which define valleys 62'). In addition, or alternatively, ridges 64' may include rings of metal, alloy, or other material embedded in membrane 60', to provide relatively more rigidity at ridges 64'. Membrane 60' may also be formed of any flexible material suitable for use in medical procedures, e.g., a silicone, a rubber, a plastic, or the like. Actuators 51a', 51b' can be operated independently. If actuator 51b' is pulled proximally relative to actuator 51a', membrane 60' will assume the configuration shown in FIG. 3D. Catheter 30 will bend in an opposite direction if actuator 51a' is pulled proximally relative to actuator 51b'. Both actuators 51a', 51b' can be pulled simultaneously a same amount, resulting in the membrane 60' expanding outward in a bulbous-liked fashion. Membrane 60' may assist to stabilize the distal end of catheter 30 within a body lumen by having ridges 64' contact the wall of the body lumen.

During actuation of accessory device 50 in FIG. 3D, one actuation wire 51a' may be pushed distally while the other actuation wire 51b' may be pulled proximally. In this instance, pushing actuation 51a' distally may cause membrane 60' to expand outward while catheter 30 is bent toward actuation wire 51b'. As membrane 60' bends, ridges 64' may contact a wall of the body. This may prevent inadvertent contact between actuation wires 51a', 51b' and the body, which may prevent injury to the body during a medical procedure.

Figure 4:
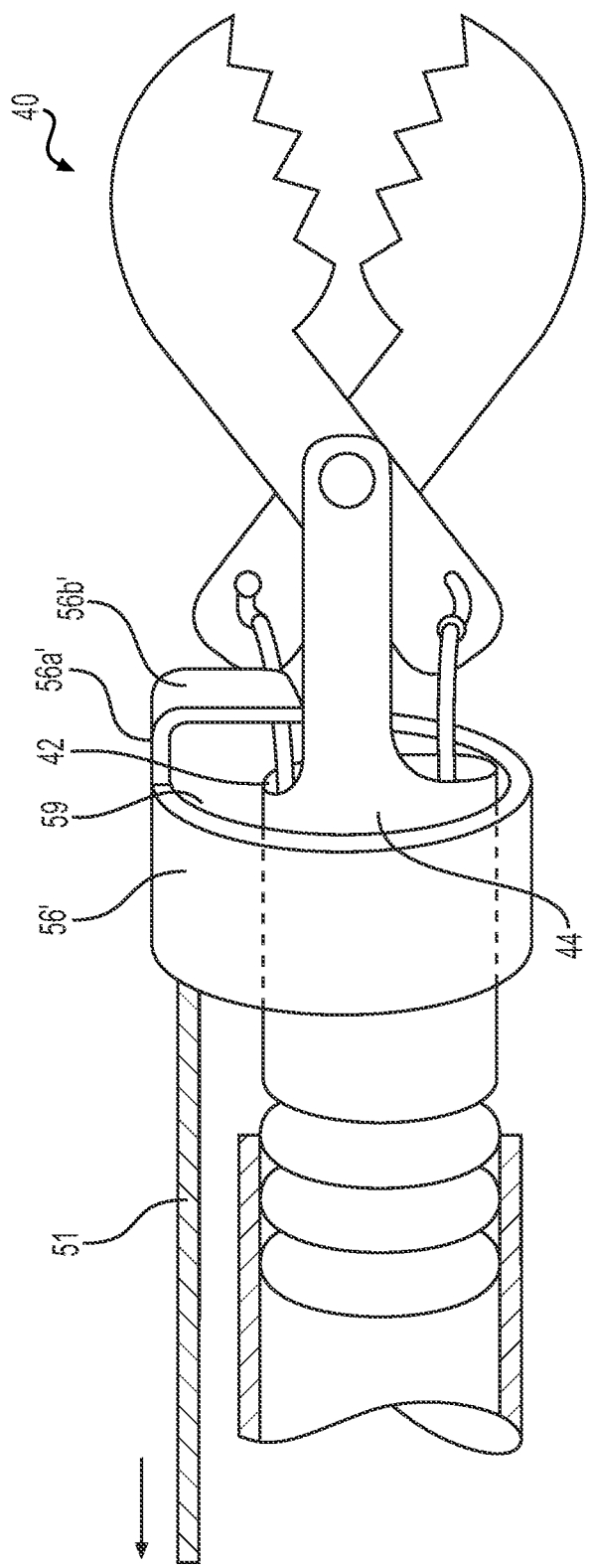
FIG. 4 is a perspective view of a distal end of an accessory device of FIG. 1 according to another embodiment.

Another example of a first cuff 56' is shown in FIG. 4. First cuff 56' is cylindrically shaped and defines a lumen 59 extending from a distal end to a proximal end of first cuff 56'. First cuff 56' includes an L-shaped protrusion, e.g., a first segment 56a' extending approximately parallel to a longitudinal axis of catheter 30 and a second segment 56b' extending approximately perpendicular to first segment 56a' and radially inward toward the central longitudinal axis. Second segment 56b' is configured to connect to a surface of end effector assembly 40. For example, second segment 56b' hooks onto a surface of end effector assembly 40 to prevent proximal movement of first cuff 56'. Second segment 56b' may engage with a stepped feature, opening, recess, or protrusion of a portion of end effector assembly 40. In the example shown in FIG. 4, additional proximal movement of first cuff 56' may cause second segment 56b' to engage (press against) a surface 42 of a clevis 44 of end effector assembly 40. Distal movement of first cuff 56' may be prevented via a friction force between catheter 30 and first cuff 56'. For example, an inner member of first cuff 56' may include a material such as the material included in inner member 54a, 56a, which may increase the friction coefficient between first cuff 56' and catheter 30.

Figure 5A:
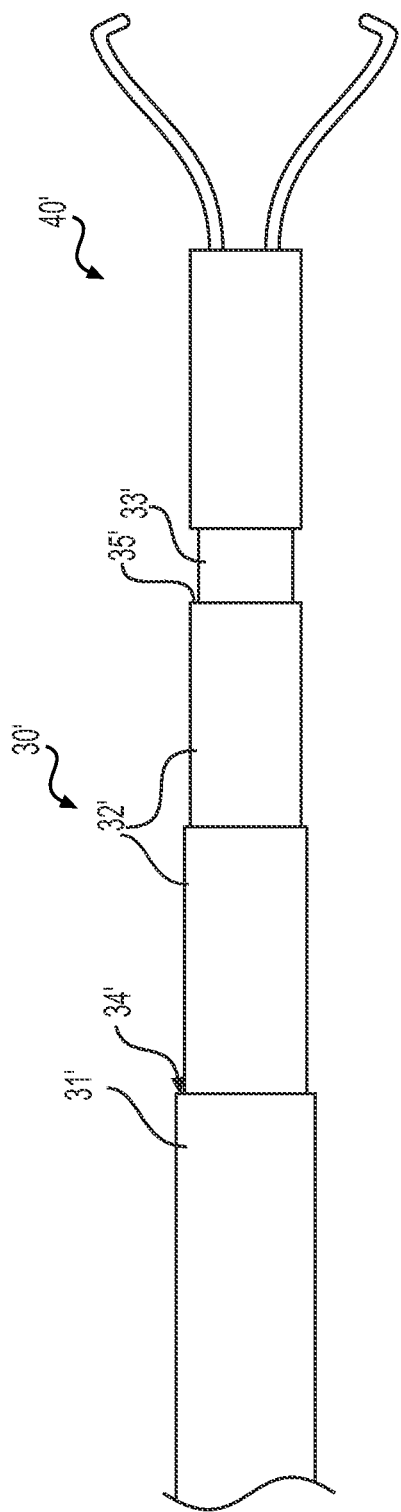
FIG. 5A is a perspective view of a medical device according to an embodiment.

FIG. 5A illustrates another example of a catheter 30' having a distal end effector 40'. Catheter 30' may include portions of different diameter, e.g., a proximal portion 31', a distal portion 33', and an intermediate portion 32' connecting proximal portion 31' to distal portion 33'. These different diameters may create transition areas between each portion. For example, a first shoulder or edge 34' is formed at the transition region between proximal portion 31' and intermediate portion 32', and a shoulder or second edge 35' is formed at the transition region between intermediate portion 32' and distal portion 33'. Edges 34', 35' provide suitable locations for attachment of cuffs of accessory device 50. For example, first cuff 56 may be attached to catheter 30' such that first cuff 56 contacts edge 35', and second cuff 54 may be attached to catheter 30' such that second cuff 54 contacts edge 34'. Alternatively, the distalmost cuff may be attached to one or more edges formed on end effector 40'. Other cuffs may be used, however, as discussed herein.

FIG. 5B illustrates a first cuff 56", which may be attached at a distal end of a catheter described herein. First cuff 56" includes a lumen 59. An annular projection 56a" extends radially inward from and approximately perpendicular to a sidewall of first cuff 56" toward a central axis of lumen 59. A projection 56c" may protrude from a surface of annular projection 56a" toward the central axis of lumen 59. Annular projection 56a" and/or projection 56c" may contact a portion of an end effector (e.g., an edge of end effector 40' in FIG. 5A) and may prevent longitudinal displacement in a proximal direction. Actuation wire 51 may be connected to an outer surface of first cuff 56" via a connector 56b". Connector 56b" may include an opening 56d" and may protrude from the outer surface of first cuff 56" and may connect to actuation wire 51 via adhesive, laser welding, crimping, or other attachment method.

FIG. 5C illustrates a second cuff 54". Second cuff 54" includes two portions connected by a hinge 54c". Hinge 54c" may be a separate member connected to each half of first cuff 54", or hinge 54c" may have a reduced amount of material so as to allow the two portions of second cuff 54" to bend relative to each other (e.g., a live hinge). A protrusion 54a" on one end of a first portion of second cuff 54" and a sloped region 54d" on one end of a second portion of second cuff 54" may clasp together to connect second cuff 54" to a medical device (e.g., catheter 30). For example, second cuff 54" may be attached to catheter 30 by connecting protrusion 54a" with sloped region 54d", e.g., protrusion 54a" may snap onto sloped region 54d". To disconnect, a force may be applied to protrusion 54a" sufficient to release protrusion 54a" from sloped region 54d". In this instance, second cuff 54" includes a single layer, e.g., second cuff 54" does not include a compressive inner layer as with second cuff 54 of FIG. 2. It will be understood, however, that additional layers, such as a compressive layer, may be used with second cuff 54".

Actuation wire 51 may be attached to an outer surface of second cuff 54" via a connector 54b". Connector 54b" may protrude from the outer surface of first cuff 54" and may connect to actuation wire 51 via adhesive, laser welding, crimping, or other attachment method. In this instance, second cuff 54" may act as the distalmost cuff of accessory device 50. In another example, actuation wire 51 may pass through an opening in connector 54b" such that actuation wire 54" may slide proximally and distally relative to second cuff 54". In this instance, second cuff 54" may be a proximal cuff of accessory device 50.

FIG. 5D illustrates a first cuff 56''', which may include a C-shaped configuration. First cuff 56''' may attach to catheter 30 via a snap fit such that first cuff 56''' may be easily removed from catheter 30 after a medical procedure. Alternatively, first cuff 56''' may be secured to catheter 30 via an adhesive, a laser welding, or other attachment means. First cuff 56''' also includes a connector 56a''' on an outer surface, which may be attached to actuation wire 51. Actuation wire 51 may pass through an opening 56b''' in connector 56a''', such that first cuff 56''' may move proximally and distally relative to actuation wire 51. Alternatively, first cuff 56''' may be fixed to actuation wire 51 to prevent relative movement. A stop 57 is provided at a distal end of actuation wire 51. Stop 57 has a larger diameter than actuation wire 51 to prevent actuation wire 51 from exiting cuff 54b'' upon proximal movement of actuation wire 51.

Figure 6:
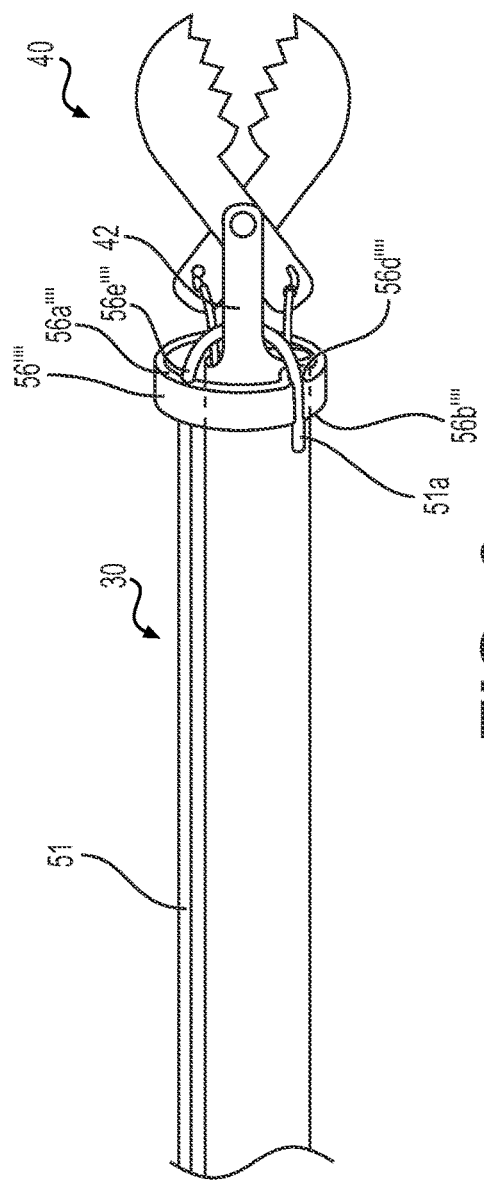
FIG. 6 is a perspective view of a distal end of a medical device according to an example.

FIG. 6 illustrates a first cuff 56''''. First cuff 56'''' may include a plurality of openings to receive actuation wire 51. Actuation wire 51 may pass through a first opening 56a'''' in first cuff 56'''' in a distal direction. Actuation wire 51 may then loop around a clevis 42 of end effector assembly 40. A distalmost end 51a of actuation wire 51 is received in a second opening 56d'''' in first cuff 56'''' and may be secured to first cuff 56''''. Second opening 56d'''' may be C-shaped or may have another geometry such that actuation wire 51 may be attached via a snap fit, an adhesive, or another suitable attachment mechanism. It will be understood that actuation wire 51 may loop around any portion of end effector assembly 40, to fixedly couple cuff 56'''' to the distal end of the medical instrument.

Figure 7:
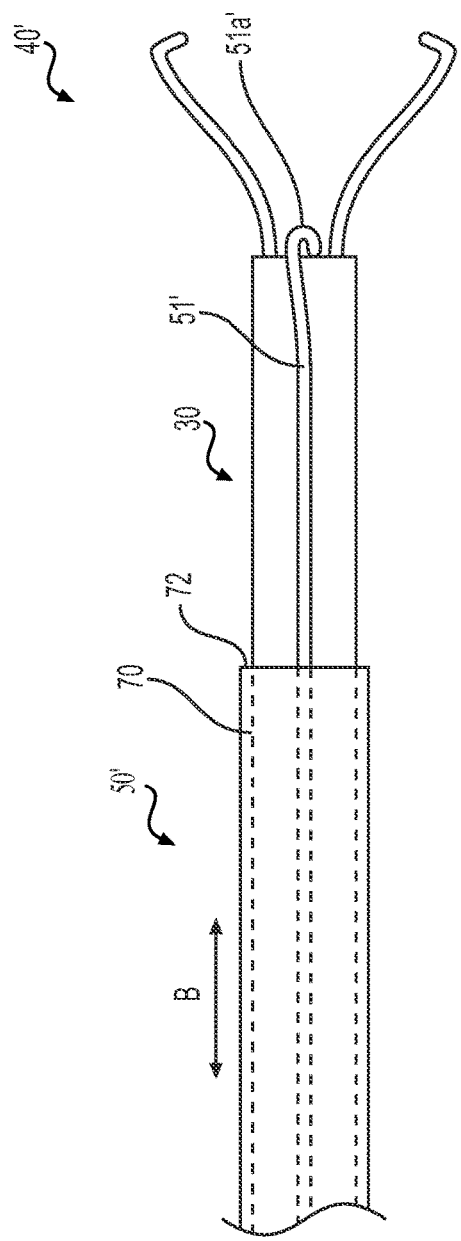
FIG. 7 is a perspective view of a distal end of a medical device according to another example.

FIG. 7 illustrates an example of an accessory device 50'. Accessory device 50' includes a sheath 70 having a lumen that slides over catheter 30. An actuation wire 51' includes a hook 51a' at a distal end. Hook 51a' is configured to grasp onto any opening, protrusion, edge, or other area suitable for connection on end effector assembly 40'. Alternatively, hook 51a' may grasp an edge of a distal end of catheter 30. In this manner, longitudinal movement of hook 51a' in a proximal direction relative to end effector assembly 40' may be prevented.

Sheath 70 may extend from a proximal handle to a position proximal of a distalmost end of catheter 30. A distance between a distal end 72 of sheath 70 and hook 51a' defines an articulation region of catheter 30. For example, distal end 72 may act as a pivot point about which the portion of catheter 30 between distal end 72 and hook 51a' bends. In this instance, a proximal movement of actuation wire 51' causes the portion of catheter 30 between hook 51a' and distal end 72 of sheath 70 to bend. Sheath 70 may be telescoping such that a position of distalmost end 72 of sheath 70 relative to hook 51a' may be changed, e.g., by two inches or less, as shown by arrow B. Changing the distance between distal end 72 and hook 51a' may allow catheter 30 to achieve larger or smaller bend radiuses. During a medical procedure, the user may move sheath 70 distally or proximally to change this distance according to a desired bend radius. Once the desired distance between distal end 72 and hook 51a' is achieved, sheath 70 may be locked by any mechanism sufficient for preventing movement of sheath 70 during the medical procedure.

According to another example, medical instrument 10 and accessory device 50 attached thereto may be introduced outside a delivery device, e.g., a scope. For example, medical instrument 10 may be attached to an outer surface of the delivery device via a rail, a cuff, or other attachment mechanism. Actuation of accessory device 50 may allow the user to bend a portion of medical instrument 10. In this manner, bending of medical instrument 10 may not be limited by a lumen of the delivery device. Additionally, or alternatively, a stability device (e.g., an inflatable balloon or other device for anchoring the delivery device within the body) may be used with the medical device and accessory device 50. The stability device may assist in inhibiting movement of the medical device when accessory device 50 is actuated and medical instrument 10 is bent.

It will be understood that, unless specifically set forth herein, any material known in the art may be used for the various elements. For example, features may include a medical grade plastic or rubber, a ceramic, a metal, or a combination thereof. It will be understood that any cuff described herein may be used as the distal cuff or the proximal cuff, unless explicitly stated otherwise. For example, endoscopes include various configurations and may be suitable to one cuff over another based on the geometry of the medical device. Further, cuffs from different embodiments may be used together, e.g., first cuff 56'''' may be used with second cuff 54, depending on the geometry of these endoscopes.

It will be apparent to those skilled in the art that various modifications and variations can be made to the disclosed device without departing from the scope of the disclosure. For example, accessory device 50 may be used with any medical instrument, with or without an associated endoscope or delivery device for introducing the medical instrument into the body. While mechanisms are disclosed for attaching cuffs 54, 56 to catheter 30, it will be understood that cuffs 54, 56 may be attached using an adhesive or the like. In this manner, accessory device 50 may provide improved and/or additional articulation of a medical instrument or tool. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An accessory device for use with a medical device, the accessory device, comprising:
    a first cuff configured to be releasably secured to a distal end of the medical device;
    a second cuff configured to be releasably secured to the medical device proximal of the first cuff;
    an actuator;
    at least one actuation wire extending from the first cuff, through the second cuff, to the actuator; and
    a membrane surrounding a portion of the medical device, wherein the membrane extends between the first cuff and the second cuff,
    wherein each of the first cuff and the second cuff includes an outer member and an inner member, and wherein the outer member includes two portions connected by a hinge so that the two portions move relative to the inner member.

2. The accessory device according to claim 1, wherein the hinge defines a pivot axis, and wherein the two portions of the outer member are configured to pivot about the pivot axis to compress the inner member against the medical device when the first cuff and the second cuff are secured to the medical device.

3. The accessory device according to claim 2, wherein a material of the inner member is configured to increase a friction between the inner member and the medical device.

4. The accessory device according to claim 2, wherein the inner member includes one or more of a gel, a foam, or a plastic, and the outer member includes one or more of a metal, a ceramic, or an elastic material.

5. The accessory device according to claim 1, wherein the membrane includes a plurality of ridges separated by valleys.

6. The accessory device according to claim 5, wherein the ridges have a first thickness and the valleys have a second thickness different than the first thickness.

7. The accessory device according to claim 1, wherein the actuator includes a slot extending along a longitudinal axis of the actuator and an actuation mechanism configured to move within the slot, wherein movement of the actuation mechanism within the slot is configured to move the at least one actuation wire proximally and distally.

8. The accessory device according to claim 7, wherein the actuation mechanism protrudes through the slot of the actuator.

9. The accessory device according to claim 1, wherein the second cuff includes an actuator lumen extending from a proximal end to a distal end, wherein the actuator lumen is configured to receive the at least one actuation wire, and wherein the second cuff defines an articulation joint about which the medical device is configured to bend.

10. The accessory device according to claim 9, wherein the at least one actuation wire is fixed to the outer member of the first cuff, and wherein the at least one actuation wire is configured to move within the actuator lumen and relative to the second cuff.

11. The accessory device according to claim 10, wherein movement of the at least one actuation wire in a proximal direction is configured to bend a portion of the medical device from a neutral position, in which the medical device lies along a longitudinal axis of the medical device, toward an articulated position angled relative to the longitudinal axis, and wherein movement of the at least one actuation wire in a distal direction is configured to move the portion of the medical device from the articulated position toward the neutral position.

12. The accessory device according to claim 1, wherein the two portions of the outer member are connected at adjacent first ends by the hinge.

13. An accessory device for use with a medical device, the accessory device, comprising:
   a first cuff configured to be secured to a distal end of the medical device;
   a second cuff configured to be secured to the medical device proximal of the first cuff;
   an actuator; and
   at least one actuation wire extending from the first cuff, through at least one actuation lumen of the second cuff, to the actuator,
   wherein the second cuff, the first cuff, and the at least one actuation wire are unsecured to the medical device in a first configuration, and wherein the second cuff, the first cuff, and the at least one actuation wire are secured to the medical device in a second configuration,
   wherein a distal end of the at least one actuation wire is fixed in a recess of the first cuff in the second configuration, and
   wherein each of the first cuff and the second cuff includes an outer member and an inner member, and wherein the outer member includes two halves configured to be detached from the inner member.

14. The accessory device according to claim 13, wherein the two halves of the outer member are connected by a hinge, and wherein the hinge defines a pivot axis.

15. The accessory device according to claim 14, wherein the two halves of the outer member are configured to rotate about the pivot axis and relative to the inner member when transitioning from the first configuration to the second configuration.

16. The accessory device according to claim 15, wherein the inner member is configured to be positioned on the medical device before the two halves of the outer member are joined together over the inner member.

17. The accessory device according to claim 13, further comprising a membrane extending from the first cuff to the second cuff and surrounding a portion of the medical device, wherein the membrane includes a plurality of ridges separated by valleys, and wherein the plurality of ridges are configured to contact a wall of a body lumen.

18. An accessory device for use with a medical device, the accessory device, comprising:
   a first cuff configured to be attached to a distal end of the medical device,
   a second cuff configured to be attached to the medical device proximal of the first cuff;
   an actuator including a channel extending along a longitudinal axis of the actuator and an actuation mechanism configured to move along the channel;
   a plurality of actuation wires extending from the first cuff, through at least one lumen of the second cuff, to the actuation mechanism,
   wherein the plurality of actuation wires are fixed to the first cuff and configured to move independently of one another relative to the second cuff, and wherein the second cuff defines an articulation joint about which the medical device is configured to bend, and
   wherein the first cuff includes (1) a ring-shaped inner member circumscribing a lumen to receive the medical device and (2) an outer member configured to move relative to the inner member.

19. The accessory device according to claim 18, further comprising a membrane extending from a proximal end of the first cuff to a distal end of the second cuff and surrounding a portion of the medical device, wherein the membrane includes a plurality of ridges.

20. The accessory device according to claim 19, wherein movement of a first wire of the plurality of actuation wires in a distal direction and movement of a second wire of the plurality of actuation wires in a proximal direction are configured to bend the membrane, and wherein the plurality of actuation wires are fixed to the first cuff via an adhesive or welding.

* * * * *